United States Patent
Thornton

(12) 
(10) Patent No.: US 6,675,802 B1
(45) Date of Patent: Jan. 13, 2004

(54) DEVICE FOR IMPROVING BREATHING INCORPORATING A DETACHABLE VENTING SEAL

(76) Inventor: W. Keith Thornton, 5524 Edlin, Dallas, TX (US) 75220

( * ) Notice: Subject to any disclaimer, the term of this patent is extended or adjusted under 35 U.S.C. 154(b) by 189 days.

(21) Appl. No.: 09/851,679

(22) Filed: May 8, 2001

(51) Int. Cl.[7] .............................................. A62B 18/08
(52) U.S. Cl. ................................................ 128/206.29
(58) Field of Search ................................ 128/136, 360, 128/848, 206.29; 433/6, 90

(56) References Cited

U.S. PATENT DOCUMENTS

| | | |
|---|---|---|
| 746,869 A | 12/1903 | Moulton |
| 774,446 A | 11/1904 | Moulton |
| 885,196 A | 4/1908 | Steil |
| 1,076,534 A | 10/1913 | Wallen |
| 1,146,264 A | 7/1915 | Kelly |
| 1,483,694 A | 2/1924 | Stukey |
| 1,649,664 A | 11/1927 | Carter |
| 1,674,336 A | 6/1928 | King |
| 2,171,695 A | 9/1939 | Harper ........................ 32/19 |
| 2,178,128 A | 10/1939 | Waite ........................ 128/136 |
| 2,424,533 A | 7/1947 | Faires ........................ 128/136 |
| 2,521,039 A | 9/1950 | Carpenter ................... 128/136 |
| 2,531,222 A | 11/1950 | Kesling ........................ 32/14 |
| 2,574,623 A | 11/1951 | Clyde ........................ 128/136 |
| 2,590,118 A | 3/1952 | Oddo, Jr. ..................... 128/136 |
| 2,627,268 A | 2/1953 | Leppich ...................... 128/136 |
| 2,833,278 A | 5/1958 | Ross ........................ 128/136 |
| 2,867,212 A | 1/1959 | Nunn, Jr. .................... 128/136 |
| 2,882,893 A | 4/1959 | Godfroy ..................... 128/136 |
| 3,107,668 A | 10/1963 | Thompson .................. 128/136 |
| 3,124,129 A | 3/1964 | Grossberg ................... 128/136 |
| 3,132,647 A | 5/1964 | Corniello .................... 128/136 |
| 3,219,033 A | 11/1965 | Wallshein ................... 128/136 |
| 3,277,892 A | 10/1966 | Tepper ..................... 128/172.1 |
| 3,312,216 A | 4/1967 | Wallshein ................... 128/136 |
| 3,321,832 A | 5/1967 | Weisberg ..................... 32/32 |
| 3,434,470 A | 3/1969 | Strickland .................. 128/136 |
| 3,457,916 A | 7/1969 | Wolicki ..................... 128/136 |
| 3,513,838 A | 5/1970 | Foderick et al. ............. 128/136 |
| 3,522,805 A | 8/1970 | Wallshein ................... 128/136 |
| 3,864,832 A | 2/1975 | Carlson ..................... 32/40 R |
| 3,871,370 A | 3/1975 | McDonald .................. 128/136 |

(List continued on next page.)

FOREIGN PATENT DOCUMENTS

| | | | |
|---|---|---|---|
| AU | 78762/94 | 9/1994 | ............ A61F/5/56 |
| DE | 156627 | 12/1904 | |
| DE | 2320501 | 4/1973 | |
| DE | 3543931 A1 | 6/1987 | .......... A61M/16/06 |
| DE | 3707952 A1 | 9/1988 | .......... A61M/16/06 |
| DE | 3719009 A1 | 12/1988 | .......... A61M/16/06 |
| DE | 19524534 C1 | 5/1996 | .......... A61M/16/04 |
| EP | 0312368 A1 | 10/1988 | ............ A61F/5/56 |
| EP | 0359135 A1 | 9/1989 | ........... A63B/71/10 |
| GB | 1569129 | 11/1980 | ............ A61F/5/56 |

OTHER PUBLICATIONS

Mayo Clinic Health Letter, vol. 13, No. 7, "Snoring," Jul. 1995.
Photocopies of 2–piece dental device manufactured by Currie–Gibson Dental Laboratory, Inc. prior to Apr. 13, 1993.
Farrar & McCarty, "A Clinical Outline of Temporomandibular Joint Diagnosis and Treatment," Normandie Study Group for TMJ Dysfunction, 3 pages, 1983.

(List continued on next page.)

*Primary Examiner*—Henry Bennett
*Assistant Examiner*—Sabrina Dagostino
(74) *Attorney, Agent, or Firm*—Baker Botts L.L.P.

(57) ABSTRACT

A device (8) for improving a user's breathing includes an oral appliance (10) and a venting seal (18) detachably coupled to the oral appliance (10). The venting seal (18) has a perimeter adapted to be placed behind the user's lips such that venting seal (18) is operable to reduce venting of a gas from the user's mouth in response to the gas being supplied to the user's nose.

33 Claims, 1 Drawing Sheet

U.S. PATENT DOCUMENTS

| | | | | |
|---|---|---|---|---|
| 3,884,226 | A | 5/1975 | Tepper | 128/136 |
| 4,016,650 | A | 4/1977 | Leusner et al. | 32/17 |
| 4,026,024 | A | 5/1977 | Tradowsky | 32/19 |
| 4,114,614 | A | 9/1978 | Kesling | 128/136 |
| 4,169,473 | A | 10/1979 | Samelson | 128/136 |
| 4,182,312 | A | 1/1980 | Mushabac | 433/68 |
| 4,227,877 | A | 10/1980 | Tureaud et al. | 433/37 |
| 4,289,127 | A | 9/1981 | Nelson | 128/207.14 |
| 4,304,227 | A * | 12/1981 | Samelson | 128/136 |
| 4,376,628 | A | 3/1983 | Aardse | 433/80 |
| 4,382,783 | A | 5/1983 | Rosenberg | 433/19 |
| 4,433,956 | A | 2/1984 | Witzig | 433/7 |
| 4,439,147 | A | 3/1984 | Magill et al. | 433/3 |
| 4,439,149 | A | 3/1984 | Devincenzo | 433/6 |
| 4,495,945 | A | 1/1985 | Liegner | 128/200.26 |
| 4,505,672 | A | 3/1985 | Kurz | 433/6 |
| 4,553,549 | A | 11/1985 | Pope et al. | 128/421 |
| 4,568,280 | A | 2/1986 | Ahlin | 433/6 |
| 4,569,342 | A | 2/1986 | von Nostitz | 128/136 |
| 4,593,686 | A | 6/1986 | Lloyd et al. | 128/136 |
| 4,602,905 | A | 7/1986 | O'Keefe, III | 433/41 |
| 4,639,220 | A | 1/1987 | Nara et al. | 433/69 |
| 4,669,459 | A | 6/1987 | Spiewak et al. | 128/136 |
| 4,676,240 | A | 6/1987 | Gardy | 128/207.14 |
| 4,715,368 | A | 12/1987 | George | 128/136 |
| 4,773,853 | A | 9/1988 | Kussick | 433/6 |
| 4,796,628 | A * | 1/1989 | Anderson | 128/360 |
| 4,799,500 | A | 1/1989 | Newbury | 128/859 |
| 4,862,903 | A | 9/1989 | Campbell | 128/861 |
| 4,901,737 | A | 2/1990 | Toone | 128/848 |
| 4,906,234 | A | 3/1990 | Voychehovski | 604/79 |
| 4,932,867 | A | 6/1990 | Ueno | 433/69 |
| 4,955,393 | A | 9/1990 | Adell | 128/859 |
| RE33,442 | E | 11/1990 | George | 128/860 |
| 5,003,994 | A | 4/1991 | Cook | 128/848 |
| 5,018,533 | A | 5/1991 | Hawkins | 128/848 |
| 5,028,232 | A | 7/1991 | Snow | 433/24 |
| 5,042,506 | A | 8/1991 | Liberati | 128/848 |
| 5,046,512 | A | 9/1991 | Murchie | 128/848 |
| 5,052,409 | A | 10/1991 | Tepper | 128/859 |
| 5,056,534 | A | 10/1991 | Wright | 128/848 |
| 5,078,600 | A | 1/1992 | Austin | 433/73 |
| 5,092,346 | A | 3/1992 | Hays et al. | 128/848 |
| 5,103,838 | A | 4/1992 | Yousif | 128/859 |
| 5,117,816 | A | 6/1992 | Shapiro et al. | 128/200.24 |
| 5,154,184 | A | 10/1992 | Alvarez | 128/848 |
| 5,154,609 | A | 10/1992 | George | 433/68 |
| 5,183,057 | A | 2/1993 | Syrop et al. | 128/845 |
| 5,188,529 | A | 2/1993 | Lüth | 433/68 |
| 5,267,862 | A | 12/1993 | Parker | 433/215 |
| 5,277,202 | A | 1/1994 | Hays | 128/848 |
| 5,313,960 | A | 5/1994 | Tomasi | 128/848 |
| 5,316,020 | A | 5/1994 | Truffer | 128/848 |
| 5,365,945 | A | 11/1994 | Halstrom | 128/848 |
| 5,373,859 | A | 12/1994 | Forney | 128/846 |
| 5,409,017 | A | 4/1995 | Lowe | 128/848 |
| 5,566,683 | A | 10/1996 | Thornton | 128/848 |
| 5,678,567 | A | 10/1997 | Thornton et al. | 128/848 |
| 5,718,244 | A | 2/1998 | Thornton | 128/864 |
| 5,720,302 | A | 2/1998 | Belfer | 128/848 |
| 5,755,219 | A | 5/1998 | Thornton | 128/201.18 |
| 5,807,100 | A | 9/1998 | Thornton | 433/48 |
| 5,829,441 | A | 11/1998 | Kidd et al. | 128/848 |
| 5,846,082 | A | 12/1998 | Thornton | 433/215 |
| 5,879,155 | A * | 3/1999 | Kittelson | 433/6 |
| 6,076,526 | A * | 6/2000 | Abdelmessih | 128/848 |
| 6,155,262 | A | 12/2000 | Thornton et al. | 128/859 |
| 6,247,926 | B1 | 6/2001 | Thornton | 433/48 |

OTHER PUBLICATIONS

Professional Positioners brochure, "Dedicated to Excellence," 4 pages, Unknown.

Great Lakes Orthodontics, Ltd., "Nocturnal Airway Patency Appliance™ (NAPA)," General Instructions, 2 pages, Not Dated.

Schmidt–Nowara, et al., "Oral Appliances for the Treatment of Snoring and Obstructive Sleep Apnea: A Review," Sleep, 81(6):501–510, 1995.

George, "Treatment of Snoring and Obstructive Sleep Apnea with a Dental Device," General Dentistry, 5 pages, Jul.–Aug. 1993.

Database WOL, Section PQ, Week 9039, Derwent Publications, Ltd., London, GB XP–002116355—Abstract "Surgical Mouth Air Duct.", 1 page, Dec. 15, 1989.

W. Keith Thornton, "Apparatus for Prevention of Snoring and Improving Breathing During Sleep," U.S. Appln. Ser. No. 08/828,623, appealed (019651.0154), Mar. 31, 1997.

W. Keith Thornton, "Device for Improved Breathing," U.S. Appln. Ser. 09/290,512, pending (019651.0174), Jan. 31, 1996.

W. Keith Thornton, "Device for Improving Breathing and Method for Fitting Same," U.S. Appln. Ser. No. 09/396,686, allowed (019651.0175), Sep. 15, 1999.

W. Keith Thornton and Andrew O. Jamieson, "Method and Apparatus for Adjusting a Dental Device," U.S. Appln. Ser. No. 08/218,719, abandoned (019651.0105), Mar. 24, 1994.

W. Keith Thornton, "Apparatus for Prevention of snoring and Improved Breathing During Sleep," U.S. Appln. Ser. No. 08/363,639, abandoned (019651.0112), Dec. 24, 1994.

W. Keith Thornton, and Andrew O. Jamieson, "Method Dan Apparatus for Adjusting a Dental Device," U.S. Appln. Ser. No. 08/435,277, abandoned (019651.0119), May 5, 1995.

* cited by examiner

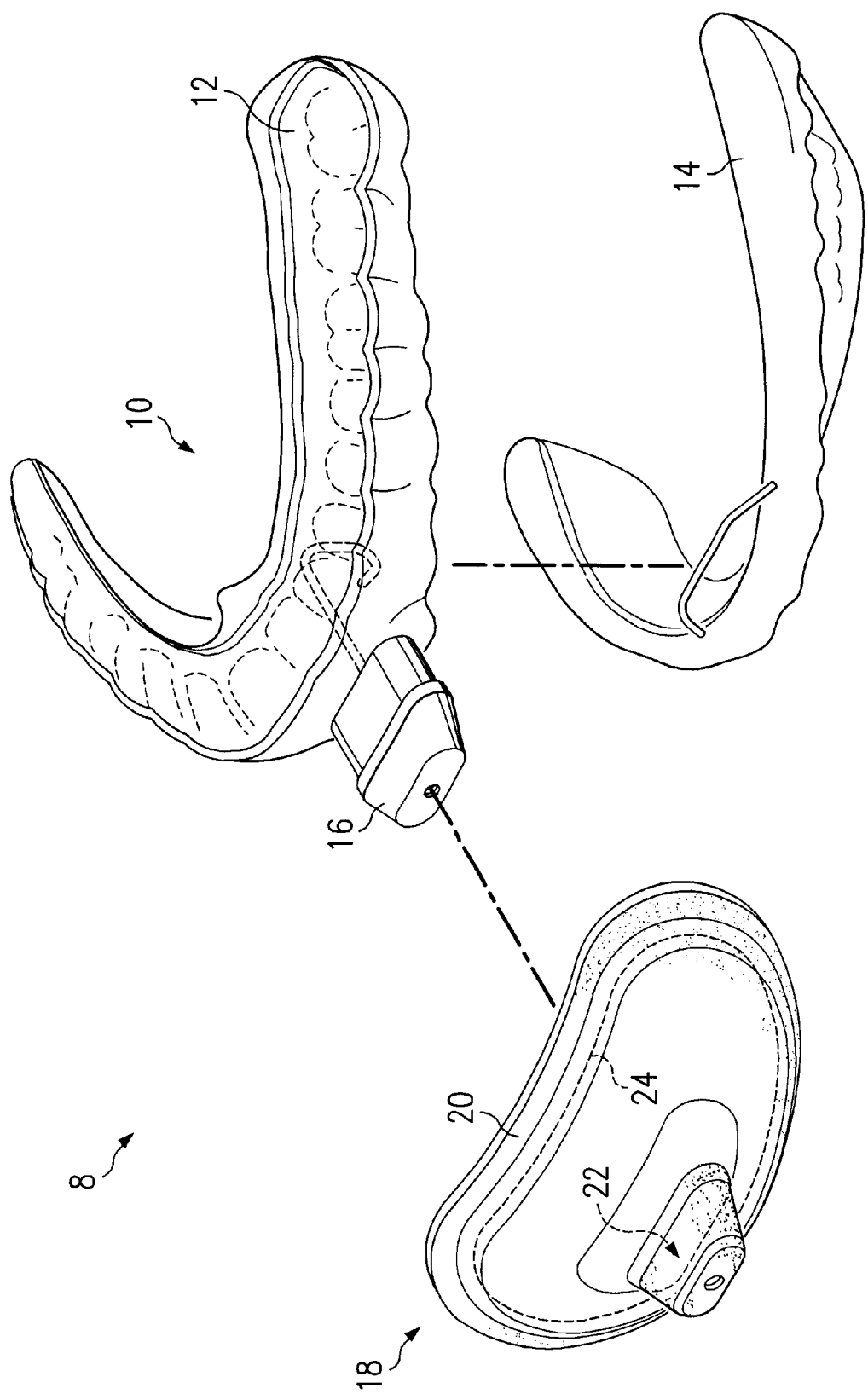

DEVICE FOR IMPROVING BREATHING INCORPORATING A DETACHABLE VENTING SEAL

TECHNICAL FIELD OF THE INVENTION

This invention relates generally to improving breathing and in particular to a device for improving breathing incorporating a detachable venting seal.

BACKGROUND OF THE INVENTION

Many people experience breathing problems on a recurring basis, which often results in difficulty sleeping, in snoring, or in other more serious conditions such as obstructive sleep apnea. One treatment for such breathing problems involves use of a device inserted into a user's mouth for extending the user's lower jaw forward. These devices help to open the user's breathing passage more fully to allow easier breathing through the user's nose and mouth. In addition or as an alternative, previous devices may include a continuous positive air pressure (CPAP) or other system for supplying a gas to the user. The gas forces the user's breathing passage open or to open more fully to improve the user's breathing. Although certain of these devices have been effective in treating breathing problems, their effectiveness may be decreased by venting of the gas from the user's mouth, reducing the gas pressure available to force the user's breathing passage open. Previous techniques for reducing venting have been inadequate for many users.

SUMMARY OF THE INVENTION

The oral appliance of the present invention reduces or eliminates problems and disadvantages associated with previous devices for improving breathing.

According to one embodiment of the present invention, a device for improving a user's breathing includes an oral appliance and a venting seal detachably coupled to the oral appliance. A perimeter of the venting seal is adapted to be placed behind the user's lips to reduce venting of a gas from the user's mouth in response to the gas being supplied to the user's nose. In a more particular embodiment, the venting seal is formed at least in part using a deformable material that may be placed in a deformable state to allow the venting seal to be customized for the user. The deformable material may include a polycaprolactone polymer.

Certain embodiments of the present invention may provide important technical advantages over previous devices for improving breathing. The present invention may be highly effective to reduce venting relative to previous devices. The venting seal may be a non-custom item or may be customized using the deformable material to fit the particular user's facial features or any other of the user's particular needs. The present invention may also allow for re-fitting of the venting seal using the deformable material, without requiring a new venting seal to be constructed. The cross-section and overall shape of the cavity of the venting seal may be such that the cavity provides a standard interface compatible with connecting posts of a variety of oral appliances. Users or clinical professionals can thus select an appropriate oral appliance for use with the venting seal, according to particular needs. Also, because the cavity may provide a standard interface, different manufacturers may produce oral appliances for use with the venting seal provided they are compatible with that standard interface.

Prior lip shields for preventing venting have required cumbersome and often intimidating head straps to secure the lip shield to the user's face, along with straps that wrap over the head and under the jaw to hold the user's jaw shut. Despite these measures, prior lip shields were still not able to achieve adequate lip competence in many cases. The present invention may overcome problems and disadvantages of such techniques. In addition, the present invention may improve the user's ability to swallow (due to the increased ease of creating negative pressure behind the venting seal or otherwise); may reduce drooling or the other undesirable effects of excess saliva exiting the user's mouth; may tend to encourage the user to breath through the user's nose (even when the device is not in use), which may improve moisture, heating, and other characteristics of the user's respiratory system; or may provide other benefits.

Other technical advantages are readily apparent to those skilled in the art from the following figures, descriptions, and claims.

BRIEF DESCRIPTION OF THE DRAWINGS

For a more complete understanding of the present invention and certain of its features and advantages, reference is made to the following descriptions taken in conjunction with the accompanying drawings, in which:

FIG. 1 illustrates an example device for improving a user's breathing that incorporates a detachable venting seal.

DESCRIPTION OF EXAMPLE EMBODIMENTS

FIG. 1 illustrates an example device 8 for improving breathing that includes an oral appliance 10 having an upper arch 12 adapted to receive at least some of a user's upper teeth and a lower arch 14 adapted to receive at least some of the user's lower teeth. Arches 12 and 14 may be any arches suitable for dental or medical uses. For example, arches 12 and 14 may be custom arches that have been customized or otherwise formed, using a suitable deformable material, to fit the definition of a particular user. Suitable deformable materials may include, for example only and without limitation, methylmethacrylate, the polycarbonate resin thermoplastic such as that sold as LEXAN, the ethylene-vinyl acetate copolymer resin sold under the name ELVAX, a thermoplastic polymer such as polycaprolactone, or any other suitable deformable material. These materials are known, at least in certain contexts, to those skilled in the art, and other suitable materials may be used without departing from the intended scope of the present invention.

In one embodiment, arches 12 and 14 are heated to temperature appropriate to place the associated deformable material in its deformable state. Arches 12 and 14 are then inserted into the user's mouth, separately or together, and the user bites down to deform deformable material into the shape of at least some of the user's teeth. Arches 12 arch 14 are removed from the user's mouth and allowed to cool and harden. Custom arches 12 and 14 may be formed in this manner by the user or a clinical professional. Arches 12 and 14 may also be formed from conventional dental casts or in any other suitable manner, according to particular needs.

Alternatively, one or both arches 12 and 14 may be non-custom arches that may themselves be adapted to receive a deformable material in which molds of at least some of the user's upper and lower teeth, respectively, may be formed. Such a deformable material may include ELVAX, a thermoplastic polymer such as polycaprolactone, or another deformable material suitable for forming molds of a user's teeth. In one embodiment, the deformable material may be heated to approximately 150° F. or another suitable temperature to place the deformable material in its deformable state. Arches 12 and 14 are then inserted into the user's mouth, separately or together, and the user bites down to deform the deformable material into the shape of at least some of the user's teeth. Arches 12 arch 14 are removed from the user's mouth and allowed to cool and harden. Non-custom arches 12 and 14 may be customized in this manner for a particular user by the user or a clinical professional.

Device 8 may be adapted for use in connection with a CPAP system, an anaesthesia system, or any other suitable system for supplying air, anaesthetic, or another gas to the user's nose. Although CPAP systems are primarily discussed, other systems for delivering a gas, at constant or varying pressures, may be used.

Upper arch 12 includes, supports, or is otherwise coupled to a connecting post 16 for detachably coupling upper arch 12 to a venting seal 18. In one embodiment, connecting post 16 may be removably coupled to upper arch 12 using a screw or other suitable fastener, although connecting post 16 may be fully or partially integral to upper arch 12 without departing from the intended scope of the present invention. Moreover, connecting post 16 may be suitable for coupling to a variety of oral appliances. For example only and not by way of limitation, connecting post 16 may be coupled to upper arch 12 (whether or not coupled to lower arch 14), to an adjustable oral appliance such as that described in U.S. Pat. No. 5,954,048, or to any other suitable oral appliance. As a result, according to the present invention, a device that incorporates a selected oral appliance may be constructed using a customized or other venting seal 18 to satisfy the user's particular needs, which provides an important technical advantage.

In general, venting seal 18 is shaped to seal behind the user's lips to reduce or substantially eliminate venting of gas from the user's mouth when device 8 is in use. Venting is known to reduce the effectiveness of continuous positive air pressure (CPAP) treatment or other treatment involving delivery of air or another gas to the user's nose at positive pressure to force the user's breathing passage open or to open more fully. When venting occurs, at least some air that would otherwise help force open the breathing passage is lost through the user's mouth. When venting is reduced, more of the gas is used to force open the breathing passage and the effectiveness of the treatment therefore increases. Venting may similarly reduce the effectiveness of anaesthesia and other applications. Those skilled in the art will appreciate that the present invention encompasses all such applications. Shell 20 of venting seal 18 may be formed from any suitable rubberized, vinyl, acrylic, plastic, or other flexible material. Venting seal 18 may be a non-custom item or may be customized to fit the particular user's facial features or any other of the user's particular needs, as described more fully below.

Cavity 22 of venting seal 18 has a cross-section and overall shape suitable to receive and engage with connecting post 16. In one embodiment, for example, connecting post 16 is force fitted into cavity 22. Moreover, as described above, in one embodiment the cross-section and overall shape of cavity 22 is such that cavity 22 provides a standard interface compatible with connecting posts of a variety of oral appliances. Users or clinical professionals can thus select an appropriate oral appliance for use with venting seal 18, according to particular needs. Furthermore, because cavity 22 may provide a standard interface, different manufacturers may produce oral appliances for use with venting seal 18 and compatible with that standard interface. Although oral appliance 10 has been described primarily as capable of extending the user's lower jaw forward, the present invention contemplates oral appliance 10 being used primarily to help secure the position of venting seal 18.

Prior lip shields for preventing venting have required cumbersome and often intimidating head straps to secure the lip shield to the user's face, along with straps that wrap over the head and under the jaw to hold the user's jaw shut. Despite these measures, prior lip shields were still not able to achieve adequate lip competence in many cases. The present invention overcomes the problems and disadvantages of such techniques. In addition, the present invention may improve the user's ability to swallow (due to the increased ease of creating negative pressure behind the venting seal 18 or otherwise); may reduce drooling or the other undesirable effects of excess saliva exiting the user's mouth; may tend to encourage the user to breath through the user's nose (even when device 8 is not in use), which may improve moisture, heating, and other characteristics of the user's respiratory system; or may provide other benefits.

In one embodiment, venting seal 18 is formed at least in part using a deformable material 24. Deformable material 24 may include one or more of the polycaprolactone polymers or other aliphatic polyesters described in U.S. Pat. Nos. 5,112,225 and 4,784,123, and also in product literature distributed by UNION CARBIDE CORPORATION. One or more polycaprolactone polymers may have the formula:

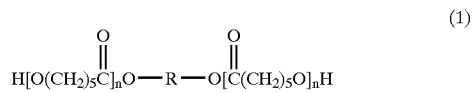

(1)

where R is an aliphatic hydrocarbon and n may range between approximately 300 to approximately 650. However, the present invention contemplates using any suitable polycaprolactone polymer, possibly including a polycaprolactone polymer with another suitable formula.

In a particular embodiment, deformable material 24 includes one or more of the TONE P-700, TONE P-767, or TONE P-787 polycaprolactone polymers manufactured by UNION CARBIDE CORPORATION, singly or in any combination. In a more particular embodiment, deformable material 24 may include approximately thirty parts by volume of TONE P-700 and sixty parts by volume of TONE P-767, together with approximately ten parts by volume of one or more other polymers, depending upon the application and particular needs. A light cured material, another polymer, or any other suitable material, such as a filler, coloring agent, stabilizer, antioxidant, or antimicrobial agent, may be used to replace or combine with a polycaprolactone polymer in forming deformable material 24 having any appropriate characteristics, properties, or uses. The present invention contemplates deformable material 24 including any suitable mixture or other combination of polycaprolactone or other polymers or other suitable materials, compounds, or compositions.

The TONE set of polycaprolactone polymers are described in U.S. Pat. Nos. 5,112,225 and 4,784,123, and in product literature distributed by UNION CARBIDE CORPORATION, as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

(2)

where R is an aliphatic hydrocarbon.

Deformable material 24 may begin as extruded pellets, beads, or rods of uniform, similar, or differing size, or in other suitable form. Deformable material 24 is heated in a microwave oven, in water or other non-solvent neutral liquid, or in any other suitable manner to between approximately 140° F. and approximately 180° F. to place deformable material 24 in its deformable state. Deformable material 24 may be maintained in this deformable state until the pellets, beads, or rods congeal, coalesce, or otherwise combine to form a deformable mass capable of assuming the shape and configuration desired. Deformable material 24 may be placed in a deformable state before, during, or after deformable material 24 is coupled to or otherwise used to form venting seal 18.

In one embodiment, deformable material 24 is applied to at least a perimeter of shell 20 so as to contact the user's teeth, gums, inner lips, or other oral structures or tissues when the perimeter of venting seal 18 is placed behind the user's lips for customized fitting. Deformable material 24 mixes, bonds, reacts, combines, or otherwise couples with the material used to form shell 20 while in a deformable state. Deformable material 24 is allowed to cool and harden to fit the particular user's oral structures and tissues. Deformable material 24 may be delivered to shell 20 while in a liquid, melted, or other deformable state by hand, using a syringe, hypodermic needle, hot glue gun, or other delivery device, or using any other suitable technique.

Venting seal 18 may remain inserted in the user's mouth or may be removed from the user's mouth before, during, or after deformable material 24 fully cools and hardens. Deformable material 24 may be used to customize venting seal 18 in the user's home, in the office of a dental, medical, or other clinical professional, or in any other suitable location. If re-fitting of venting seal 18 becomes necessary or desirable, deformable material 24 may be reheated to again place deformable material 24 in a deformable state, the perimeter of venting seal 18 may again be placed behind the user's lips to conform to the user's oral structures and tissues, and deformable material 24 may be allowed to again cool and harden in a new (and presumably more desirable) shape. Providing re-fitting of venting seal 18 using deformable material 24, without requiring a new venting seal 18 to be constructed, provides an important technical advantage.

Although the present invention has been described above in connection with several embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A device for improving a user's breathing, comprising:
   an oral appliance comprising an arch adapted to receive at least some of the user's teeth to secure the oral appliance in position in the user's mouth; and
   a venting seal detachably coupled to the arch of the oral appliance, the venting seal having a perimeter adapted to be placed behind the user's lips such that the venting seal is operable to reduce venting of a gas from the user's mouth in response to the gas being supplied to the; user's nose while the user's teeth are positioned in the arch of the oral appliance and the venting seal is coupled to the arch of the oral appliance.

2. The device of claim 1, wherein the venting seal comprises a cavity adapted to receive a post of the oral appliance.

3. The device of claim 2, wherein the post is force fitted into the cavity.

4. The device of claim 2, wherein the cavity has a cross-section and overall shape such that the cavity provides a standard interface suitable for being detachably coupled to one of a plurality of oral appliances that each comprise a post.

5. The device of claim 1, wherein the venting seal is operable to reduce venting independent of any strap to secure the venting seal in position.

6. The device of claim 1, wherein the venting seal comprises a shell and a deformable material that is coupled to the shell and may be placed in a deformable state to allow the venting seal to be customized for the user.

7. The device of claim 6, wherein the deformable material comprises a polycaprolactone polymer.

8. The device of claim 6, whew the deformable material is chemically bonded to at least the perimeter of the venting seal.

9. The device of claim 1, wherein the gas is supplied to force open the user's breathing passage.

10. The device of claim 1, wherein the gas is supplied for purposes of anesthesia.

11. The device of claim 1, wherein the venting seal is further operable to reduce an amount of excess saliva allowed to escape the user's mouth.

12. The device of claim 1, wherein the oral appliance comprises an upper arch adapted to receive at least some of the user's upper teeth and a lower arch adapted to receive at least some of the user's teeth, the upper arch adapted to be coupled to the lower arch so as to place the lower arch in a fixed forward position.

13. A device for improving a user's breathing, comprising:
   first means for receiving at least some of the user's teeth to secure the first means in position in the user's mouth; and
   second means, detachably coupled to the first means, for reducing venting of a gas from the user's mouth in response to the gas being supplied to the user's nose while the user's teeth are positioned in the first means and the second means is coupled to the first means, the second means having a perimeter adapted to be placed behind the user's lips.

14. A device for improving a user's breathing, comprising:
   an upper arch adapted to receive at least some of the user's upper teeth and to secure the upper arch in position in the user's mouth, the upper arch comprising a post; and
   a venting seal detachably coupled to the post of the upper arch, the venting seal comprising a cavity adapted to receive the post of the upper arch, the venting seal further comprising a shell having a perimeter adapted to be placed behind the user's lips such that the venting seal is operable to reduce venting of a gas from the users mouth in response to the gas being supplied to the user's nose while the user's teeth are positioned in the upper arch and the venting seal is coupled to the post of the upper arch, the venting seal further comprising a deformable material chemically bonded to at least the perimeter of the shell to allow the venting seal to be customized for the user.

15. The device of claim 13, wherein the second means comprises a cavity adapted to receive a post of the first means.

16. The device of claim 15, wherein the post is force fitted into the cavity.

17. The device of claim 15, wherein the cavity has a cross-section and overall shape such that the cavity provides a standard interface suitable for being detachably coupled to one of a plurality of first means that each comprise a post.

18. The device of claim 13, wherein the second means is operable to reduce venting independent of any strap to secure the second means in position.

19. The device of claim 13, wherein the second means comprises a shell and a deformable material that is coupled to the shell and may be placed in a deformable state to allow the second means to be customized for the user.

20. The device of claim 19, wherein the deformable material comprises a polycaprolactone polymer.

21. The device of claim 19, wherein the deformable material is chemically bonded to at least the perimeter of the second means.

22. The device of claim 13, wherein the gas is supplied to force open the user's breathing passage.

23. The device of claim 13, wherein the gas is supplied for purposes of anesthesia.

24. The device of claim 13, wherein the second means is further operable to reduce an amount of excess saliva allowed to escape the user's mouth.

25. The device of claim 13, wherein the first means comprises an oral appliance comprising an upper arch adapted to receive at least some of the user's upper teeth and a lower arch adapted to receive at least some of the user's teeth, the upper arch adapted to be coupled to the lower arch so as to place the lower arch in a fixed forward position.

26. The device of claim 14, wherein the post is force fitted into the cavity.

27. The device of claim 14, wherein the cavity has a cross-section and overall shape such that the cavity provides a standard interface suitable for being detachably coupled to one of a plurality of upper arches that each comprise a post.

28. The device of claim 14, wherein the venting seal is operable to reduce venting independent of any strap to secure the venting seal in position.

29. The device of claim 14, wherein the deformable material comprises a polycaprolactone polymer.

30. The device of claim 14, wherein the gas is supplied to force open the user's breathing passage.

31. The device of claim 14, wherein the gas is supplied for purposes of anesthesia.

32. The device of claim 14, wherein the venting seal is further operable to reduce an amount of excess saliva allowed to escape the user's mouth.

33. The device of claim 1, wherein the oral appliance further comprises a lower arch adapted to receive at least some of the user's teeth the upper arch adapted to be coupled to the lower arch so as to place the lower arch in a fixed forward position.

* * * * *